(12) United States Patent
Thacker

(10) Patent No.: US 6,344,332 B1
(45) Date of Patent: Feb. 5, 2002

(54) METHODS FOR THE RAPID DETECTION OF ACTIVELY RESPIRING MICROORGANISMS

(75) Inventor: James Thacker, Manassas, VA (US)

(73) Assignee: Thaco Research, Ltd., Chantilly, VA (US)

( * ) Notice: Subject to any disclaimer, the term of this patent is extended or adjusted under 35 U.S.C. 154(b) by 0 days.

(21) Appl. No.: 09/148,491

(22) Filed: Sep. 4, 1998

Related U.S. Application Data

(60) Provisional application No. 60/057,657, filed on Sep. 5, 1997.

(51) Int. Cl.$^7$ .................. C01N 33/53; C12Q 1/00; C12Q 1/26; C12Q 1/02; C12Q 1/22
(52) U.S. Cl. .......... 435/7.1; 435/7.2; 435/7.32; 435/7.9; 435/7.92; 435/7.94; 435/4; 435/25; 435/29; 435/31; 435/34; 435/968
(58) Field of Search ............... 435/4, 25, 29, 435/31, 34, 968, 7.1, 7.2, 7.32, 7.9, 7.92, 7.94

(56) References Cited

U.S. PATENT DOCUMENTS

| 4,026,767 A | * | 5/1977 | Shih et al. | |
| 4,728,608 A | | 3/1988 | Roberts et al. | 435/34 |
| 5,168,063 A | | 12/1992 | Doyle et al. | 435/240.27 |

FOREIGN PATENT DOCUMENTS

| EP | 0 429 794 | * | 6/1991 | |
| EP | 0429794 A2 | | 6/1991 | G01N/33/569 |
| JP | 5-207895 | * | 8/1993 | |

OTHER PUBLICATIONS

Database WPI, Week 9103, Derwent Publications Ltd., London, GB; AN 91–020477; Gazenko et al., "Controlling cultivation of microortganisms—uses specified tetrazolium salts as specific substrates, and dehydrogenase activities as indicators".

International Search Report forPCT/US98/18588, dated Jun. 14, 1999.

Antibodies, A Laboratory Manual; Harlow and Lane, Cold Spring Harbor Laboratory, 1986.*

Bovill R. Comparison of the Fluorescent Redox Dye 5–Cyano–2,3–ditolyltetrazolium Chloride with p–Iodonitrotetrazolium Violet to Detect Metabolic Activity in Heat Stressed Listeria monocytogenes Cells. J of Applied Bacteriology 77(4)353–358, Apr. 1994.*

Kumar S. Oxido–reductive Functions of Entamoeba histolytica in Relation to Virulence. Ann of Tropical Med and Para 86(3)239–248, 1992.*

* cited by examiner

*Primary Examiner*—Mark Navarro
*Assistant Examiner*—Padma Baskar
(74) *Attorney, Agent, or Firm*—Heller Ehrman

(57) ABSTRACT

A method for the rapid detection of actively respiring microorganisms comprises the steps of detecting the presence of microorganisms utilizing microbial enzymatic conversion of tetrazolium salts to formazan products, detecting the presence of formazan product.

28 Claims, 4 Drawing Sheets

METHODS FOR THE RAPID DETECTION OF ACTIVELY RESPIRING MICROORGANISMS

This appln claims benefit of Prov. No. 60/057,657 filed Sep. 5, 1999.

BACKGROUND OF THE INVENTION

1. Field of the Invention

This invention is directed to the methods for rapid amplification and detection of actively respiring microorganisms. Such methods are useful in the detection of microbial contaminants in the environment, industrial systems, water purification systems, as well as clinical, food, cosmetic and pharmaceutical samples.

2. Description of the Background

Many U.S. industrial and medical business sectors are at risk for economic loss from microbial contamination. The presence of microorganisms can have a negative impact on business efficiency and productivity. Many bacterial species implicated in human disease as well as those non-pathogenic species that adversely impact industrial processes are ubiquitous in aqueous environments of all types including lakes, rivers, ponds, industrial process waters and even potable water supplies. The total potential economic loss to the U.S. gross domestic product due to microbial contamination has been estimated to be $1–$2 Trillion (THACO Corporation, Independent Market Research, 1993).

Three primary determinants for monitoring microorganism contamination in industrial processes are (i) determination of the quantity of microorganisms that are present, (ii) determination that there are no microorganisms present, and (iii) determination of the specific type (species) of microorganisms that are present.

The classical approach to determinants (i) and (ii) is to culture the sample in question in the presence of selective nutrients and microscopically examine a specimen after staining with specific reagents. Whereas this approach may be satisfactory for some definitive clinical examinations, it is necessary to provide rapid detection, enumeration and identification of microorganisms in industrial and other routine and non-routine medical examinations such as mass casualty or epidemic situations.

Modern methods for microorganism detection and enumeration have focused on the development of more sensitive methods of detecting microorganisms and to a lesser extent upon methods for amplification of the number of microorganisms present in the sample to be analyzed. Some of the technologies in current practice include DNA probes, RNA probes, ATP measurements, immunoassays, enzymatic assays, and respirometic measurements. Many of these tests do not rapidly detect less than $10^5$ cfu/mL or still require complicated or lengthy amplification procedures to increase the concentration of the substrate being detected. Enhancement of the sensitivity of the detection system reduces the threshold concentration of microorganisms to be detected and consequently reduces the time required for amplification. These enhanced assay methods include fluorimetric, radiometric and photometric methods.

For instance, Schapp (U.S. Pat. No. 4,857,652) identified compounds that can be triggered by an activating agent to produce light. This luminescent reaction is used for ultra sensitive detection of phosphatase-linked antibodies and DNA probes. At least one such application of this technology has been commercialized as Photo Gene manufactured by Life Technologies, Inc. (Gaithersburg, Md.). Similarly, Abbas and Eden (U.S. Pat. No. 5,223,402) identify a method that uses 1,2-dioxetane chemiluminescent substrates linked to either alkaline phosphatase or β-D-galactosidase. Theoretically, their method can detect microorganism concentrations as low as 1–100 cfu/mL.

Another strategy for the enhancement of microbial detection is the utilization of fluorescence based detection systems. For example, Fleminger (Eur. J. Biochem. 125:609–15, 1982) used a fluorescent amino benzoyl group that was intra molecularly quenched by a nitrophenylalanyl group. In the presence of bacterial aminopeptidase P, the nitrophenylalanyl group is cleaved and the fluorescence of the sample increases proportionately. A wide variety of other enzymes have been assayed by similar procedures and include hydrolases, carboxypeptidases and endopeptidases. As is the case with the chemiluminescence based assays, fluorescence based assays are susceptible to interferences from chemical quenching agents typical in industrial process waters, require specialized equipment and operator training. Additionally, the fluorescent reagents themselves may be highly toxic and therefore unsuitable for some applications.

Although applicable in certain limited laboratory settings, chemiluminescent methods such as these are susceptible to interference from a variety of chemical quenching agents commonly found in industrial process waters, environmental water sources and biological matrices. Moreover, the methods, as taught in the above referenced patents, require specialized technical training of the user, specialized equipment, multiple steps in the conduct of the assay and enrichment of the microorganism concentration. Taken together, such considerations lengthen the total assay time, raise the capital costs and make this technology unsuitable for high volume, high throughput applications.

Species typing, referred to as determinant (iii) above, not only requires amplification of the microorganisms present, but also requires the selective detection of only the species of interest in the presence of background microflora. The classic approach to species typing is to selectively amplify the presence of the organism of interest through a pre-enrichment step followed by a selective enrichment step using a nutrient specific media followed finally by biochemical or serological confirmation. The time required for these procedures can be as long as six to seven days which is clearly outside the realm of practicality for use in industrial laboratories or high throughput clinical laboratories.

One strategy that has recently been commercialized is the GENE-TRAK™ calorimetric assay (GENE-TRAK Systems, Inc. Framingham, Mass.). This technology attempts to simultaneously exploit an amplification strategy and an enhancement of the detection system's sensitivity. The approach is an alternative to other approaches that use probes directed against chromosomal DNA. Instead, the GENE-TRAK system targets ribosomal RNA (rRNA) which is present in 1,000–10,000 copies per actively metabolizing cell. A unique homologous series of nucleotides, approximately 30 nucleotides in length and containing a poly-dA tail, is hybridized with the unique rRNA sequence in the target organism. This probe is referred to as the capture probe. A second unique probe of 35–40 nucleotides is labeled at the 3' and the 5' ends with fluorescein. This probe is the detector probe and binds to a region of the rRNA adjacent to the capture probe. After hybridization, bound complexes are captured on a solid support coated with poly-dT which hybridizes with the poly-dA tail of the capture probe. The rRNA-detector probe complex is detected with polyclonal anti-fluorescein antibody conjugated to horseradish peroxidase. This complex is then reacted with the enzyme substrate, hydrogen peroxide, in the presence of tetramethylbenzidine. The blue color that develops is proportional to the amount of rRNA captured.

Blackburn reviewed the development of rapid alternative methods for microorganism typing as it pertains to the food industry (C. de W. Blackburn, "Rapid and alternative methods for the detection of salmonellas in foods," Journal of Applied Bacteriology, 75:199–214, 1993). Therein, Blackburn describes several techniques for detection of Salmonella that rely upon a selective pre-enrichment and enrichment approach to amplification, the best of which still required approximately six hours before detectable levels of Salmonella were present. Enhanced detection methods were also reviewed and included measurements of metabolism, immunoassays, fluorescent-antibody staining, enzyme immunoassay, immunosensors, bacteriophages and geneprobes. Analysis times could be reduced to as short as 20 minutes; the detection limits were about $10^5$ cfu (Blackburn et al., "Separation and detection methods for salmonellas using immunomagnetic particles," Biofouling 5:143–156, 1991). Similarly the detection limits could be reduced to as low as 1–10 cfu, however the enrichment protocols required 18–36 hours. In all cases, the described methods provided detection limits that were either too high or analysis times that were too long to be practical for application to industrial processes and high volume, high throughput clinical situations.

There have been numerous approaches to microorganism detection and typing. For instance, U.S. Pat. No. 4,376,110 describes a solid-phase immunoassay employing a monoclonal capture antibody and a labeled secondary antibody. Alternatively, U.S. Pat. No. 4,514,508 utilizes labeled complement and U.S. Pat. Nos. 4,281,061; 4,659,678; and 4,547,466 describe other immunological based variants. All of these methods require from $10^3$ to $10^7$ cfu/mL to reliably detect the target microorganism. Necessarily, additional enrichment steps are required which add several hours to days to the assay procedure.

Various enrichment techniques are described as well. For instance Valkirs (U.S. Pat. No. 4,727,019) and Hay-Kaufman (U.S. Pat. No. 4,818,677) describe flow-through devices to capture cells and in situ immunoassay to detect the presence of the target organism. Schick (U.S. Pat. No. 4,254,082) describes an ion exchange particle system for capturing the target organism and Chau (U.S. Pat. No. 4,320,087) describes an activated charcoal coated bead capture device. All of these devices suffer several limitations such as small volume capacities, fouling from the presence of particulates in the sample or nonspecificity of the capture process and are as a consequence unsatisfactory for large volume, high throughput industrial and clinical applications.

While it has been shown that a number of technologies have been developed for a variety of applications, it is also clear that there continues to be a need for the development of simple, sensitive, rapid, inexpensive and reliable detection systems with applicability to the broad scope of industrial and clinical processes.

SUMMARY OF THE INVENTION

The present invention overcomes the problems and limitations of current methods for rapid detection and enumeration of microorganisms such as bacteria by providing methods for amplification of the presence of microorganisms in a sample without reliance upon pre- or post-enrichment processes. The present invention also provides for the highly sensitive, quantitative enumeration of total viable microorganisms with a detection limit less than 1000 cfu/mL and an analysis time less than two hours. The present invention is amenable to the analysis of clinical, food, cosmetic, pharmaceutical, industrial and environmental samples without regard to the sample matrix. It is clear to one skilled in the art that the net effect of these embodiments provides a sensitive and fast microorganism-detection technology.

Advantages of the invention are set forth, in part, in the description which follows and, in part, will be obvious from this description and may be learned from the practice of this invention.

DESCRIPTION OF THE INVENTION

Figure 1:
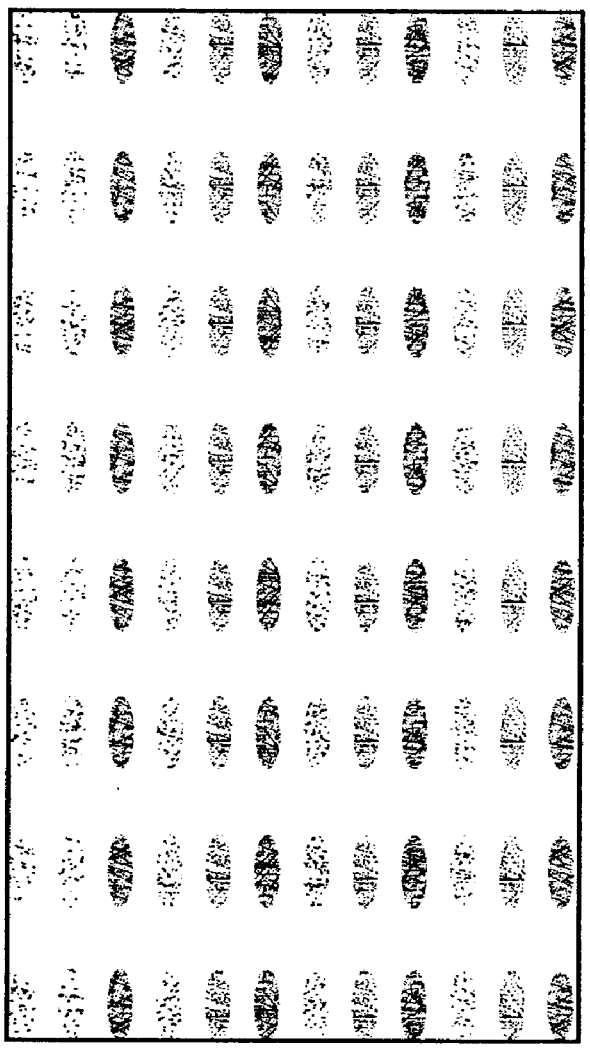
FIG. 1 Visual detection of bacteria using a dot blot format on a nitrocellulose support.

As embodied and broadly described herein, the present invention is directed to methods for the general amplification of the presence of and thereby detection of viable microorganisms. As described in the following embodiments, it is clear to those skilled in the art that the present invention may also be used as a method for detecting the presence of most microorganisms including pathogenic microorganisms in clinical, environmental and food samples and, as such, is a valuable diagnostic tool for the sub-clinical diagnosis of infectious disease. For example, the present invention can be used to amplify and detect the presence of bacteria, fungus, parasites or other eukaryotic microorganisms such as virus-infected cells (wherein the virus imparts a specific enzyme activity to infected cells as compared to uninfected cells) in blood, tissue, tissue homogenate, bodily fluid or other clinical samples, thereby assisting in the diagnosis of a particular disease. These methods may be used to specifically detect the presence of one or a small number of metabolic activities (e.g. one or more enzymes), or generally detect the presence of any metabolic activity (e.g. any microbial enzymes) in a particular sample to provide assurances of the presence or absence of a specific microorganism (e.g. a virus-infected cell or a parasite), or the presence or absence of any microorganisms (e.g. sterility or the presence of sterilized conditions).

The present invention is directed to a process for amplifying or viability-marking the presence of total viable microorganisms in a sample. As used herein, the term "amplify" or "amplifying" microorganisms and/or the presence of microorganisms refers to a process whereby microorganisms are induced to form a marker, as described below, thereby facilitating the detectability of the presence of the microbes. One method of the present invention involves, first, trapping actively respiring microorganisms on the surface of a filtration membrane. To then amplify or viability-mark (which is also referred to as biomarking) the microorganisms that may be present in a sample, a microbial-enzyme substrate (viability substrate) is added in a nutrient media and taken up by the actively respiring microorganisms on the filtration membrane surface. The viability substrate is then metabolized by the microorganisms to a single water-insoluble marker molecule. This marker molecule or viability marker accumulates rapidly and in direct proportion to the number of microorganisms present in the sample.

After an incubation period which may be from minutes to hours to days, and is preferably less than about twenty four hours, less than about eight hours, less than about two hours, and more preferably less than about thirty minutes, microorganisms are digested in a manner to produce cell fragments with the viability marker adsorbed to the surfaces of the cellular debris. Primary antibodies specific to the viability marker are added to the sample and affinity adsorbed to the surface of the cellular debris. Secondary antibodies, specific for the primary antibodies, are conjugated to a reporter molecule (e.g. enzyme, luminescent protein, radioisotope, fluorescent dye and the like, as well as combinations), and are affinity adsorbed to the primary antibodies. The reporter molecule is quantitatively detected either directly or indirectly after the addition of the appropriate activator or enzyme substrate.

Accordingly, one embodiment is directed to a method for amplifying the presence of actively respiring microorganisms in a sample comprising contacting the contents of the sample to a nutrient medium containing a predetermined amount of a viability substrate, wherein metabolism of the viability substrate by the microorganisms of said sample produces a viability marker. The viability substrate is preferably a tetrazolium salt which is metabolized by the microorganism to produce a water insoluble marker molecule that accumulates in direct proportion to the number of microorganisms in the sample.

Tetrazolium salts that can be added to viable microorganisms to produce a detectable marker after metabolism by the microorganisms include triphenyltetrazolium, nitrotetrazolium blue, iodonitrotetrazolium or dimethyl thiazolyldiphenyl tetrazolium. The predetermined amount of tetrazolium salt is between about 0.01 mg/mL and 10.0 mg/mL, preferably from about 0.1 to about 1.0 mg/mL, and more preferably from about 0.2 to about 0.6 mg/mL. Viability substrates useful in the practice of the invention include a nutrient and a reducing agent. In the preferred embodiment, the nutrient media contains glucose (as the nutrient) and NADH (as the reducing agent). As is clear to those skilled in the art, other nutrient sources such as other carbohydrates are well known and can be used as well as other known reducing agents.

The present invention is also directed to methods for detecting an actively respiring microorganisms in a sample. One such method comprises amplifying the presence of the actively respiring microorganisms as described above, digesting the amplified microorganisms, contacting a primary antibody prepared against a substituted formazan with the digested microorganisms, contacting a secondary antibody prepared against the primary antibody, the secondary antibody being conjugated to a reporter molecule, and detecting the reporter molecule. This method may further comprise the step of trapping the actively respiring microorganisms on a solid filtration membrane before or after amplification. The reporter molecule or label may be an enzyme, a bioluminescent protein, a radioisotope, a chemiluminescent dye, a visible dye, a latex particle, a magnetic particle, a fluorescent dye or a combination thereof.

Another embodiment is directed to a method for detecting an actively respiring microorganisms in a sample comprising the steps of trapping the microorganisms on a solid filtration membrane, amplifying the presence of the microorganisms by the method of the present invention; digesting the amplified microorganisms, contacting primary antibodies prepared against a substituted formazan with the digested microorganisms, thereby capturing the primary antibodies, contacting secondary antibodies prepared against the primary antibodies, each of the secondary antibodies being conjugated with a detectable reporter marker, and detecting the secondary antibodies that are bound to the captured primary antibodies.

The present invention is also directed to a method for detecting amplified microorganisms comprising digesting the amplified microorganisms; incubating the digested microorganisms with a primary antibody specific for the viability marker, conjugating the primary antibody to a reporter molecule to form a reporter-primary antibody complex, and detecting the reporter molecule.

Other embodiments of the invention involve methods where the primary antibodies are immobilized. One such method of detecting microorganisms comprises digesting microorganisms amplified by the method of the present invention by incubating them with a lysozyme to form cellular debris, immobilizing primary antibodies specific for the viability marker on a solid support, contacting the digested microorganisms with the immobilized primary antibodies thereby capturing the microorganisms, and detecting the presence of the viability marker.

In this embodiment, the step of detecting may comprise contacting the captured digested microorganisms with a reporter antibody prepared from the primary antibody, the reporter antibody being conjugated to a detectable marker, and detecting the reporter antibodies that bind to the captured digested microorganisms. Alternatively, the step of detecting may comprise detecting the captured viability marker by detecting a change in a physical, a chemical, an optical, or an electrical property of the solid support. In this latter embodiment, the primary antibodies are preferably immobilized on a solid sensor surface.

Another similar embodiment is directed towards the detection of the amplified viability marker wherein the marker, which is adsorbed to surfaces of the digested cellular debris, is affinity captured onto a solid support by immobilized primary antibodies. The marker is further amplified by incubation with the primary antibody conjugated to a reporter molecule (e.g. enzyme, luminescent protein, radioisotope, fluorescent dye and the like as well as one or more combinations of such labels), to form a primary antibody-antigen-reporter antibody sandwich. The reporter molecule is then quantitatively detected either directly or indirectly after the addition of the appropriate activator or enzyme substrate.

Another embodiment of the invention is directed towards the production of antibodies that are specifically reactive to the marker substance of the present invention. Said antibodies may be polyclonal or monoclonal and can be obtained from most any mammalian species or recombinantly synthesized. The monoclonal or polyclonal antibodies are preferably prepared to a substituted formazan and cross reactive to other formazans.

The present invention is also directed to kits for the rapid and sensitive detection and enumeration of viable microorganisms in a sample. These kits contain the components needed for an unskilled person to test a sample for the presence of viable microorganisms. Kits comprise one or a plurality of containers for obtaining and holding a sample of fluid. Containers may be useful for obtaining sample from a body of liquid such as water, a bodily tissue or fluid, or another fluid source. Kits may also contain a filter or other membrane which is used to remove larger particles from the sample, a solid support for absorbing microorganisms within the sample, a chemical biomarker such as tetrazolium salt to be added to the suspected microorganisms of the sample, and primary and secondary antibodies as described herein one or both of which may be labeled with detectable labels.

The present invention is also directed to a method for diagnosing a disease due to a microorganism comprising amplifying the presence of the microorganisms by the methods of the invention, digesting the amplified microorganisms using lysozyme, alkali or another chemical lysing agent, contacting a primary antibody prepared against a substituted formazan with the microorganisms or remaining cellular debris, contacting a secondary antibody prepared against the primary antibody, the secondary antibody being conjugated to a reporter molecule and detecting the reporter molecule.

Still another embodiment is directed to a method for quantitating actively respiring microorganisms in a sample comprising contacting said microorganisms to a nutrient medium containing a predetermined amount of a viability substrate, such as a tetrazolium salt; metabolizing the viability substrate to a viability marker using the microorganisms forming a quantitative amount of the viability marker that reflects the quantity of actively respiring microorganisms in the sample and detecting the viability marker.

The methods disclosed herein are useful in the detection of a single species of microorganisms or a mixed population of microorganisms, and can be used to reliably detect microorganisms in samples containing less than 1000 cfu/mL in less than two hours. As will be clear to those of ordinary skill in the art, the methods disclosed herein can be used to detect microorganisms in various types of samples, including clinical samples, food samples, cosmetic samples, pharmaceutical samples and industrial samples or an environmental samples. With respect to clinical samples, the methods of the invention are useful in connection with testing blood samples, tissue samples, tissue homogenate samples, or bodily fluid samples, among others.

The following examples are offered to illustrate embodiments of the invention and should not be viewed as limiting the scope of the invention.

EXAMPLES

Example 1

MicroDot Assay

A standard mixture of bacteria (Bacillus 12%; Cedecea<1%; Citrobacter 19%; Enterobacter 5%; Escherichia 23%; Klebsiella 2%; Kluyvera 23%; Pseudomonas 1%; Providencia 3%; Salmonella 5%; Serratia 7%; Staphylococcus<1%: all percentages are approximate) was prepared to give samples containing 10 cfu/mL to 100,000 cfu/mL in decade increments. An 8×12 cm piece of $0.2\mu$ nitrocellulose was divided into an 8×12 array of wells with an ELIFA template (Pierce Chemical Company). A 200 $\mu$L sample or control was applied with a multichannel pipette. Wells of lane 1 were a reagent blank consisting only of a sample containing 10,000 cfu/mL bacteria and to which no Substrate Buffer (see below) was added. Lane 2 wells were negative controls of sterile 1% BSA. Lane 3 wells were positive controls of the antigen-BSA conjugate at a concentration of 50 $\mu$g/mL. Wells of lanes 4–6 contained samples with a bacteria concentration of 1,000 cfu/mL, 10,000 cfu/mL and 100,000 cfu/mL respectively. Wells in lanes 7–9 contained samples with bacteria concentrations of 100 cfu/mL, 1,000 cfu/mL and 10,000 cfu/mL respectively. Wells in lanes 10–12 contained samples with bacteria concentrations of 10 cfu/mL, 100 cfu/mL and 1,000 cfu/mL respectively.

A vacuum was applied to the ELIFA system and samples and controls were pulled through the membrane to a waste trap. Substrate Buffer was prepared by dissolving 0.5 mg/mL 3-[4,5-dimethylthiazol-2-yl]-2,5-diphenyltetrazolium salt (MTT) and 792 $\mu$g/mL NADH in trypticase soy broth nutrient media and 200 $\mu$L was applied to all wells except those of lane 1 (reagent blank) and lane 3 (positive control). The timing of Substrate Buffer addition was controlled so that wells of lanes 4–6 incubated a total of 30 minutes, those of lanes 7–9 incubated 60 minutes and those of lanes 10–12 incubated a total of 90 minutes. All incubations were carried out at 37° C.

After incubation the Substrate Buffer was removed by vacuum filtration. Digestion Buffer was prepared by adding 0.5 mg/mL lysozyme and 1.86 mg/mL EDTA in 25 mM Tris buffered saline, pH 8 (0.9% NaCl) and 200 $\mu$L was added to all wells except those of lane 3 (positive control) and incubated 15 minutes at 37° C. After incubation the Digestion Buffer was removed by vacuum filtration and the wells were washed by five successive additions/filtrations with 400 $\mu$L portions of Blocking Buffer (0.1% Tween-20 in 25 mM Tris buffered saline, 0.9% NaCl, pH 8). Between the third and fourth washes, the wells were incubated for approximately 15 minutes with the Blocking Buffer at room temperature.

After blocking the nitrocellulose membrane was removed from the ELIFA apparatus. A three-step development process was performed by incubating the nitrocellulose membrane in a 10 mL bath of primary antibody to a substituted formazan and cross reactive to other formazans diluted 1:500 with Dilution Buffer (1% BSA in 25 mM Tris buffered saline, 0.9% NaCl, pH 8). Incubation was carried out for one hour at room temperature. The membrane was transferred to a bath containing 10 mL of Blocking Buffer and incubated for another 15 minutes. The membrane was rinsed with 10 mM phosphate buffered saline (0.9% NaCl) pH 7.2.

The membrane was transferred to the secondary antibody bath (goat anti-rabbit IgG conjugated to alkaline phosphatase, Pierce Chemical Co.) containing 10 mL of secondary antibody diluted 1:2,500 with Dilution Buffer. The membrane was incubated for one hour at room temperature in this bath. After incubation the wash cycle described above was repeated.

The third and final step of the development process was incubation of the membrane with BCIP/NBT substrate (Pierce Chemical Co.). This substrate is prepared just prior to use by diluting each reagent stock 1:10 with 10 mL of 0.1 M Tris buffer, pH 8. The membrane was incubated in the substrate bath until dot color development was satisfactory (approximately 30 minutes). The reaction was stopped by washing the membrane with deionized water. The results are presented in FIG. 1.

Example 2

Antigen Capture ELISA

The standard bacteria mixture of Example 1 was prepared to give samples containing 10 cfu/mL to 10,000,000 cfu/mL in decade increments. Sample (200 $\mu$L) was added to sterile bullet tubes arranged in a 7×8 array. 20 uL of concentrated (10×) Substrate Buffer (see Example 1 above) was added to each tube except the tubes in the last column which were designated as reagent blank control samples. The tubes of row A contained sterile media and were designated as negative controls. These tubes were incubated for one hour at 37° C. After incubation 20 uL of concentrated (10×) Digestion Buffer (see Example 1 above) was added and the samples and controls were incubated at room temperature for 30 minutes.

A 100 μL portion of each sample and control was transferred to a 96-microwell plate containing covalently bound primary antibody. A 100 μL sample of antigen-BSA complex (50 μg/mL) was added to a column of empty wells as a positive control. The samples and controls were incubated for another hour at 37° C. After the incubation samples were removed by aspiration and the wells were washed with 400 μL of Wash Buffer (0.01% Tween-20 in 25 mM Tris buffered saline, 0.9% NaCl, pH 8) per well in five successive wash/aspiration cycles. Between the third and fourth cycle, wells were incubated with Wash Buffer for 3 minutes at room temperature.

Figure 2:
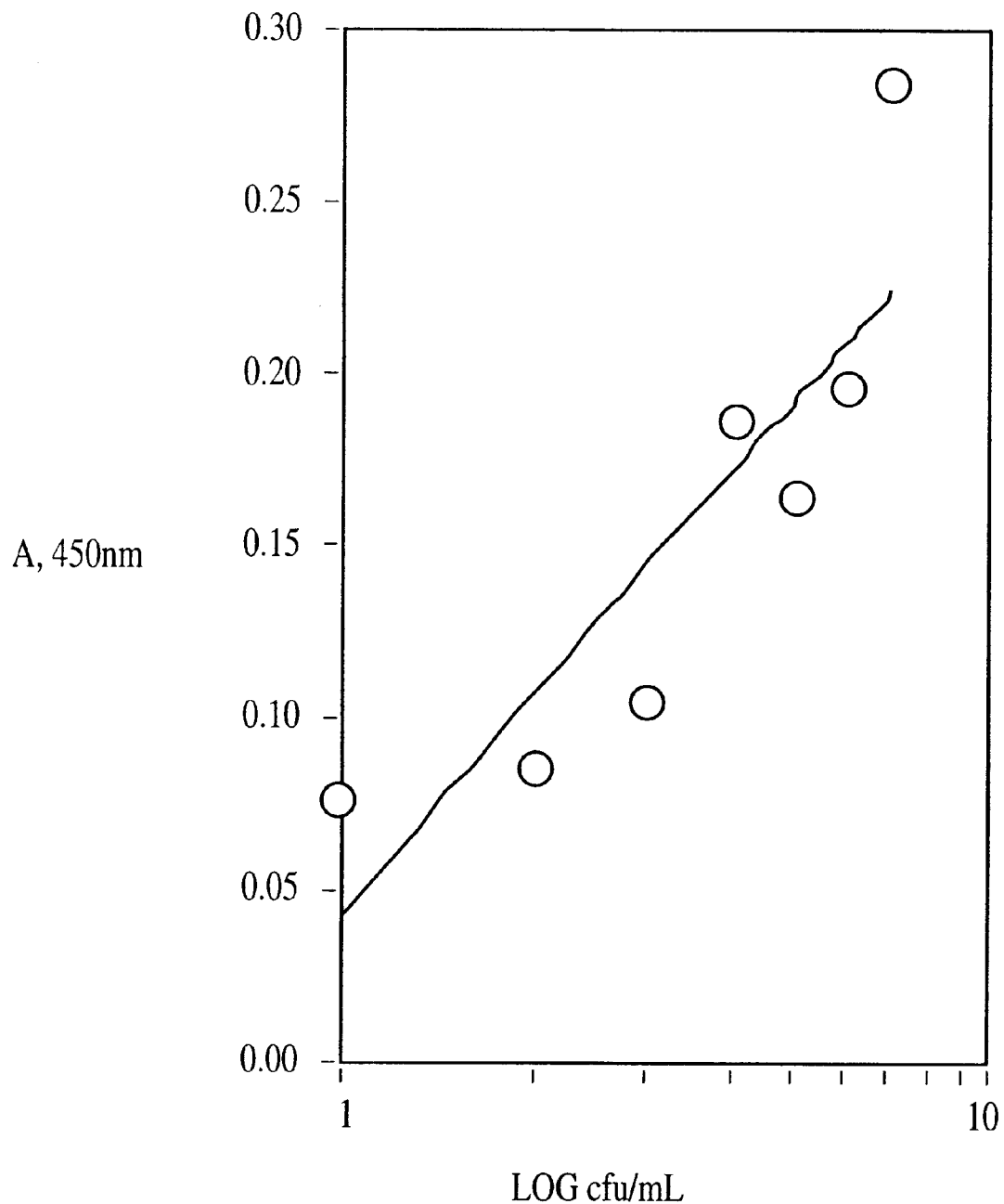
FIG. 2 Antigen capture ELISA of bacteria concentrations from 10 cfu/mL to 10,000,000 cfu/mL.

Primary antibody was conjugated to horseradish peroxidase to form a reporter antibody complex. Reporter antibody was diluted 1:5,000 in Dilution Buffer (see Example 1) and 100 μL was transferred to each well of the microplate and incubated at room temperature for one hour. After incubation the reporter antibody was removed by aspiration and the wells of the microplate were washed in the manner described above. Slow TUB® substrate (100 μL, Pierce Chemical Co.) was added to each well and the plate incubated 30 minutes. The reaction was stopped by the addition of 50 μL of 1 M sulfuric acid and the absorbance at 450 nm in each well was read in the MRX-HD (Dynex Technologies, Inc.) 96-well microplate reader. The results are presented in FIG. 2.

Example 3

Bioluminescence Assay

The standard bacteria mixture of Example 1 was prepared to give samples containing 10 cfu/mL to 1 billion cfu/mL in decade increments. Sample or control (200 μL) was added to each well of a sterile 8×12 Durapore® (Millipore Corporation) microfilter plate. Wells in column 1 received no sample and were background blanks. Wells of column 12 received sterile growth media and were negative controls. The wells of column 2 received a sample containing a bacteria concentration in excess of 1 billion cfu/mL as a positive control. The remaining wells in columns 3–11 received sample replicates containing bacteria concentrations from 10 cfu/mL to $10^9$ cfu/mL in decade increments. Each sample and control was therefore replicated eight times.

All wells were immediately evacuated by vacuum filtration and 200 μL of Substrate Buffer (see Example 1) was added to each well except those in column 1. The plate was incubated for 15 minutes at 37° C. and again the wells were evacuated by vacuum filtration. Digestion Buffer (200 μL, see Example 1) was added to each well except those of column 1 and the plate was incubated 15 minutes at room temperature on a rotating mixer. After incubation the wells were evacuated by vacuum filtration and each well was washed with 3 consecutive 400 μL portions of AquaLite® (Sea Lite Sciences, Inc.) wash buffer (20 mM Tris, 5 mM EDTA, 0.15 M NaCl, 0.05% Tween-20, 15 mM sodium azide, pH 7) with vacuum evacuation between each wash.

Primary antibody was diluted 1:500 in Dilution Buffer (see Example 1) and 200 μL was added to each well including those of column 1. The plate was incubated one hour at 37° C. and the primary antibody was removed by vacuum filtration. Each well was washed in the manner as described earlier.

AquaLite® secondary antibody (goat, anti-rabbit IgG conjugated to Aqueorin, Sea Lite Sciences, Inc.) was diluted 1:100 in AquaLite® Assay Buffer (25 mM Tris, 10 mM EDTA, 2 mg/mL BSA 0.15 M KCl, 0.05% Tween-20, 15 mM sodium azide, pH 7.5) and 200 μL was added to each well of the microfilter plate. The plate was incubated 30 minutes at room temperature on a rotating mixer. After incubation the contents of the wells were removed by vacuum filtration and washed in the manner described earlier.

Figure 3:
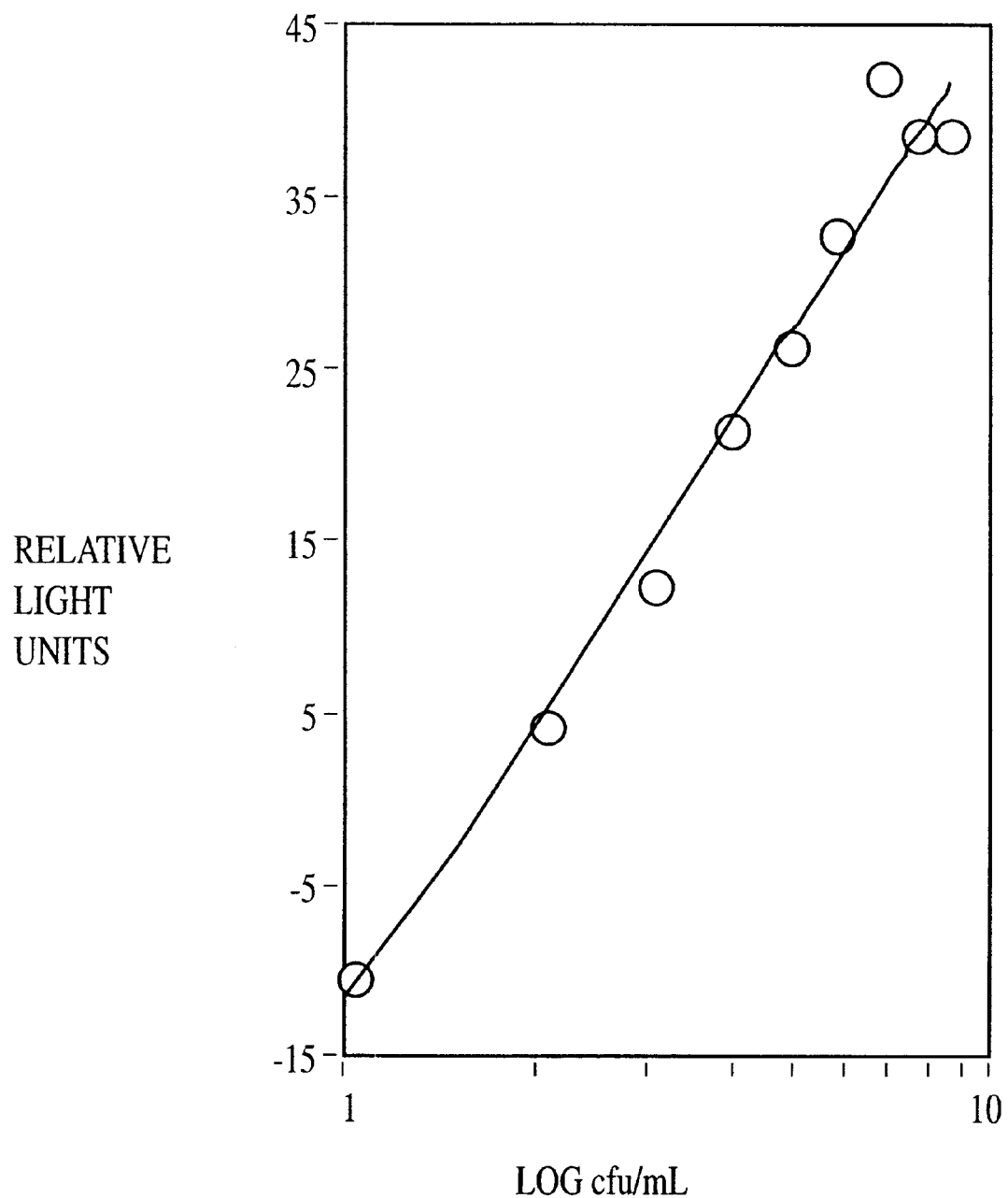
FIG. 3 Bioluminescence assay of samples containing bacteria concentrations from 10 cfu/mL to 1 billion cfu/mL.

Flash luminescence readings were taken using a MLX Luminometer (Dynex Technologies, Inc. The total integral of relative light units was summed over a one second read time per well after the automatic addition of 200 μL of AquaLite® Trigger Buffer (50 mM Tris, 10 mM calcium acetate, 15 mM sodium azide, pH 7.5). The microfilter plate was maintained at a constant 35° C. during the data acquisition phase. These results are presented in FIG. 3.

Example 4

Chemiluminescence Assay

The standard bacteria mixture of Example 1 was prepared to give samples containing from nominally 10 cfu/mL to 10,000 cfu/mL in decade increments. Sample or controls (100 μL) was added to each well of a sterile 8×12 SilentScreen® (Nalge Nunc International) microfilter plate. Wells in column 1 received no sample and were background blanks. Wells of column 12 received sterile growth media and were negative controls. The wells of column 2 received a sample containing nominally 1 million cfu/mL as a positive control. The remaining wells in columns 3–11 received sample replicates containing bacteria concentrations from 10 cfu/mL to 1 million cfu/mL.

All wells were immediately evacuated by vacuum filtration and 100 μL of Substrate Buffer (0.5 mg/mL 3-[4,5-dimethylthiazol-2-yl]-2,5-diphenyl-tetrazolium chloride (MTT), 792 μg/mL NADH and 30 mg/mL Trypticase Soy Broth dissolved in 10 mL of deionized water and sterile filtered) were added to each well except those in column 1. The plate was incubated for 15 minutes at room temperature on a rotating mixer and again the contents of the wells were evacuated by vacuum filtration. Digestion Reagent was prepared by dissolving 0.5 mg/mL Lysozyme in Buffer A (0.5% BSA, 25 mM Tris, 0.15 M NaCl, 10 mM EDTA, 15 mM sodium azide, pH 7.0). Digestion Reagent (100 μL) was added to each well except those of column 1 and the plate was incubated a second time for 15 minutes at room temperature on a rotating mixer. After incubation, the well contents were evacuated by vacuum filtration and each well was washed with a single 400 μL portions of Wash Buffer (0.5% BSA, 0.05% Tween-20, 25 mM Tris, 0.15 M NaCl, 15 mM sodium azide, pH 7.5) and the contents evacuated by vacuum filtration.

The lyophilized primary antibody was reconstituted with 1.1 mL of 50% glycerol and further diluted 1:100 in Buffer A. 100 μL of the diluted antibody were added to each of the wells except those of column 1 and the plate was incubated at room temperature on an orbital mixer for 30 minutes. After incubation, the contents of the wells were evacuated by vacuum filtration and washed with three consecutive 400 μL portions of Wash Buffer with vacuum filtration between each wash.

Secondary antibody-alkaline phosphatase conjugate (goat, anti-rabbit IgG, Pierce Chemical Co.) was reconstituted according to manufacturers directions and diluted 1:5000 in Buffer B (0.5% BSA, 25 mM Tris, 0.15 M NaCl, 1 mM $MgCl_2$, 0.1 mM $ZnCl_2$, 15 mM sodium azide, pH 7.2). 100 μL of the diluted antibody were added to each of the wells except those of column 1 and the plate was incubated at room temperature for 30 minutes on a rotating mixer. Following the incubation step the contents of the wells were evacuated by vacuum filtration and washed in the manner described for the primary antibody.

Figure 4:
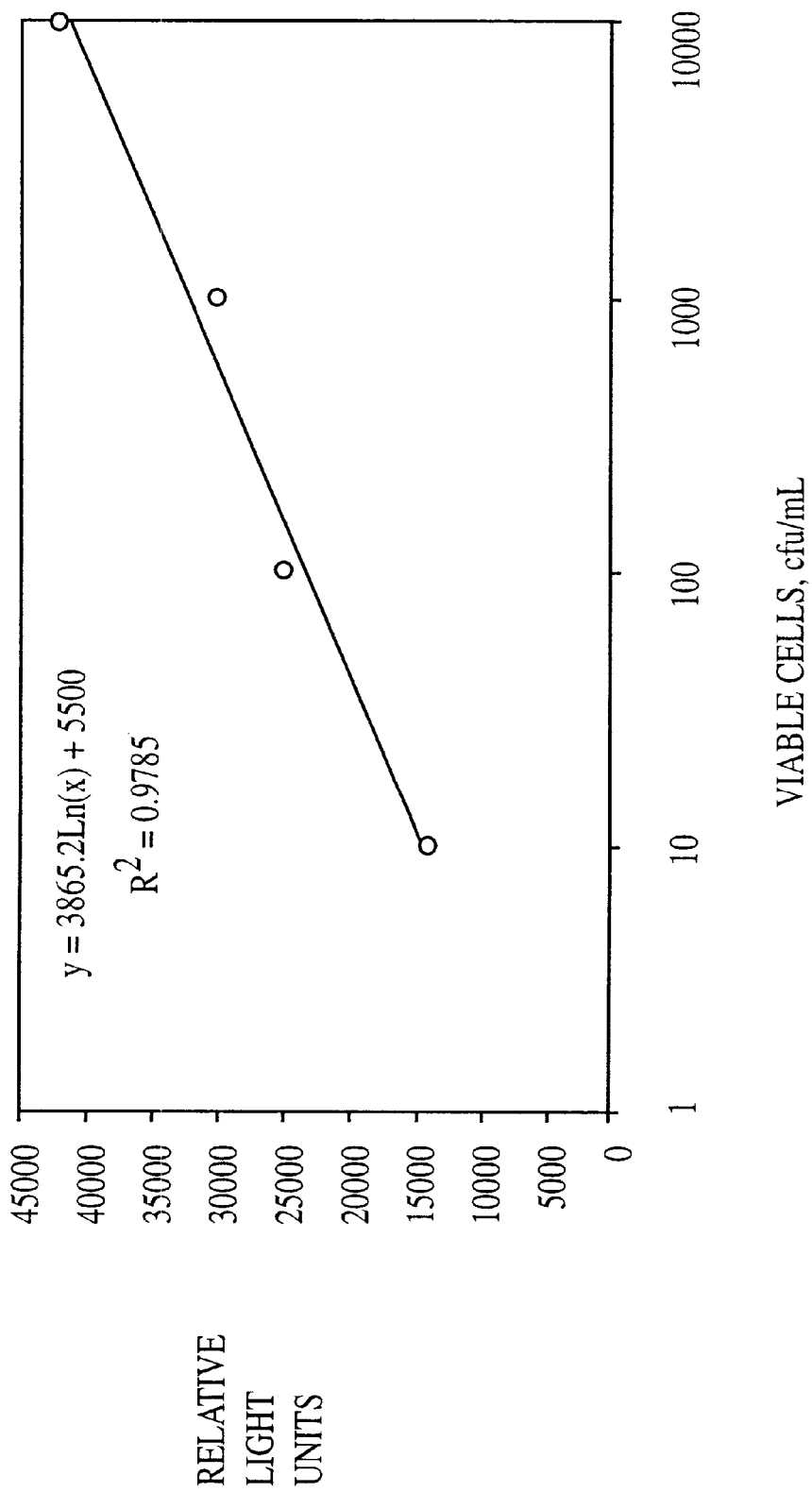
FIG. 4 Chemiluminescent assay and samples containing bacteria concentrations from 10 cfu/mL to 10,000 cfu/mL.

Chemiluminescent substrate (Lumiphos 530, Lumigen, Inc.) was added to all wells and the plate was incubated for 45 minutes at 37° C. After the incubation, the contents of the filter plate were filtered into an opaque white 96-well capture plate (Nalge Nunc International) using a vacuum filtration manifold. Luminescence readings were taken using a MLX Luminometer (Dynex Technologies, Inc.). The total integral of relative light units per well was summed over a one second read interval at ambient temperature. The results are presented in FIG. 4.

Other embodiments and uses of the invention will be apparent to those skilled in the art from consideration of the specification and practice of the invention disclosed herein. All U.S. patents and other documents cited herein including U.S. Provisional patent application Ser. No. 60/057,657, entitled "A New Method for the Rapid Detection and Enumeration of Total Viable Bacteria and Species Typing," filed Sep. 5, 1997, are specifically incorporated by reference. It is intended that the specification and examples be considered exemplary only, with the true scope and spirit of the invention being indicated by the following claims.

I claim:

1. A method for detecting the presence of less than 1000 cfu/mL of viable, actively respiring microorganisms in a sample comprising:

contacting said sample to a nutrient medium containing a predetermined amount of a microbial-enzyme substrate;

allowing the microorganisms to metabolize said substrate;

enzymatically digesting the microorganisms; and detecting the presence of the metabolized substrate and correlating with the known standard, wherein said detecting comprises contacting said digested microorganisms with a primary antibody to said metabolized substrate.

2. The method of claim 1 wherein the microorganisms comprise bacteria.

3. The method of claim 1 wherein the metabolized microbial-enzyme substrate comprises triphenyltetrazolium, nitrotetrazolium blue, iodonitrotetrazolium or dimethylthiazolydiphenyl tetrazolium.

4. The method of claim 1 wherein the nutrient medium contains glucose and NADH.

5. The method of claim 1 wherein the metabolized substrate is a water insoluble marker that accumulates in said microorganisms in direct proportion to the number of microorganisms in said sample.

6. The method of claim 1 wherein the metabolized substrate comprises an enzyme, a bioluminescent protein, a radioisotope, a chemiluminescent dye, a visible dye, a latex particle, a magnetic particle or a fluorescent dye.

7. The method of claim 1 wherein the sample is a clinical sample, a food sample, a cosmetic sample, a pharmaceutical sample, an industrial sample or an environmental sample.

8. The method of claim 7 wherein the clinical sample is a blood sample, a tissue sample, a tissue homogenate sample or a bodily fluid sample.

9. The method of claim 1 wherein the microorganisms comprises a single species of microorganisms or a mixed population of microorganisms.

10. The method of claim 1 further comprising the step of trapping the actively respiring microorganisms on a solid support.

11. The method of claim 10 wherein the solid support is a filtration membrane.

12. The method of claim 10 wherein detecting comprises detecting the metabolized substrate by a change in one or more physical, chemical, optical or electrical properties.

13. The method of claim 1 wherein the sample contains less than 1000 cfu/mL.

14. The method of claim 1 wherein the sample contains less than 100 cfu/mL.

15. The method of claim 1 wherein the sample contains less than 10 cfu/mL.

16. The method of claim 1 wherein detecting takes less than two hours.

17. The method of claim 1 wherein the sample contains less than 100 cfu/mL and detecting takes less than two hours.

18. The method of claim 1 wherein the primary antibody is an antibody prepared against a substituted formazan.

19. The method of claim 1 wherein enzymatically digesting comprises incubating the microorganisms with a lysozyme.

20. The method of claim 1 wherein the metabolized substrate is adsorbed on a surface of the digested microorganisms.

21. The method of claim 20 wherein the primary antibody is conjugated to a reporter molecule and detecting further comprises:

incubating the digested microorganisms with the primary antibody conjugated to the reporter molecule, thereby forming a primary antibody-antigen-reporter molecule sandwich; and detecting the reporter molecule.

22. The method of claim 20 wherein detecting further comprises:

incubating the digested microorganisms with the primary antibody;

conjugating the primary antibody to a reporter molecule to form a reporter molecule-primary antibody complex; and detecting the reporter molecule.

23. The method of claim 20 wherein the primary antibodies are immobilized on a solid support such that the metabolized substrate is captured during contacting said digested microorganisms with the immobilized primary antibody.

24. The method of claim 23 wherein detecting further comprises:

contacting the captured metabolized substrate with a reporter antibody prepared against the primary antibody, the reporter antibody being conjugated to a detectable marker; and detecting the reporter antibodies that bind to the captured viability marker.

25. The method of claim 23 wherein detecting further comprises detecting the captured metabolized substrate by detecting a change in a physical, a chemical, an optical, or an electrical property.

26. The method of claim 20 wherein detecting further comprises:

contacting the digested microorganisms and primary antibody with secondary antibodies prepared against the primary antibodies and conjugated with a detectable marker; and detecting the secondary antibodies that are bound to the primary antibodies.

27. The method of claim 20 wherein detecting further comprises:

contacting the digested microorganisms and primary antibody with a secondary antibody prepared against the primary antibody, the secondary antibody being conjugated to a reporter molecule; and detecting the reporter molecule.

28. The method of claim 27 wherein the reporter molecule comprises an enzyme, a bioluminescent protein, a radioisotope, a chemiluminescent dye, a visible dye, a latex particle, a magnetic particle or a fluorescent dye.

* * * * *